(12) United States Patent
Konrad et al.

(10) Patent No.: US 10,772,494 B1
(45) Date of Patent: Sep. 15, 2020

(54) SYSTEMS AND METHODS FOR REDUCING EYE-RELATED ABERRATIONS

(71) Applicant: Facebook Technologies, LLC, Menlo Park, CA (US)

(72) Inventors: Robert Konrad, Redmond, WA (US); Marina Zannoli, Seattle, WA (US); Douglas Robert Lanman, Bellevue, WA (US); Kavitha Ratnam, Kirkland, WA (US); Yusufu Njoni Bamaxam Sulai, Bothell, WA (US)

(73) Assignee: Facebook Technologies, LLC, Menlo Park, CA (US)

(*) Notice: Subject to any disclaimer, the term of this patent is extended or adjusted under 35 U.S.C. 154(b) by 13 days.

(21) Appl. No.: 16/014,415

(22) Filed: Jun. 21, 2018

Related U.S. Application Data

(60) Provisional application No. 62/645,764, filed on Mar. 20, 2018.

(51) Int. Cl.
*A61B 3/00* (2006.01)
*A61B 3/103* (2006.01)
*A61B 3/113* (2006.01)
*A61B 3/10* (2006.01)
*A61B 3/14* (2006.01)

(52) U.S. Cl.
CPC .......... *A61B 3/0008* (2013.01); *A61B 3/103* (2013.01); *A61B 3/1005* (2013.01); *A61B 3/113* (2013.01); *A61B 3/0025* (2013.01); *A61B 3/1015* (2013.01); *A61B 3/14* (2013.01)

(58) Field of Classification Search
CPC ..... A61B 3/0008; A61B 3/103; A61B 3/1005; A61B 3/113; A61B 3/14; A61B 3/0025; A61B 3/1015
USPC ......................................... 351/200, 205, 221
See application file for complete search history.

(56) References Cited

U.S. PATENT DOCUMENTS

2018/0364482 A1* 12/2018 Georgiou ........... G02B 27/0172

OTHER PUBLICATIONS

Claudio M. Privitera et al., "Eye-tracking technology for real-time monitoring of transverse chromatic aberration," Optics Letters, v.41, n.8, pp. 1728-1731.

* cited by examiner

Primary Examiner — Tuyen Tra
(74) Attorney, Agent, or Firm — FisherBroyles, LLP

(57) ABSTRACT

The disclosed system may include (1) a light source that generates light for an image, (2) an optical subsystem that (a) receives the generated light from the light source, and (b) generates, based on the received light, converging light defining an exit pupil that includes the image, where the exit pupil is smaller than a pupil of an eye of a viewer, and (3) a control subsystem that controls at least one of the light source or the optical subsystem to reduce aberration of the image that is caused by the eye of the viewer. Various other methods, systems, and computer-readable media are also disclosed.

20 Claims, 6 Drawing Sheets

SYSTEMS AND METHODS FOR REDUCING EYE-RELATED ABERRATIONS

CROSS REFERENCE TO RELATED APPLICATION

This application claims the benefit of priority to U.S. Provisional Application No. 62/645,764, filed 20 Mar. 2018, the disclosure of which is incorporated, in its entirety, by this reference.

BACKGROUND

The human eye may produce optical aberrations, in which the cornea, lens, and other portions of the eye that constitute the human optical system cause light entering the eye to not be properly focused on the retina, producing a blurring of the resulting image. Generally, aberrations fall into two categories: monochromatic aberrations (e.g., defocus, astigmatism, spherical aberration, and so on), which may result in improper focusing of portions of light having different wavelengths and which may be caused by the geometry (e.g., location, shape, orientation, etc.) of various portions of the eye, and chromatic aberrations (e.g., axial aberrations and lateral aberrations), which may result in different portions of light having different wavelengths being focused at different locations within the eye.

In some cases, chromatic aberrations may be caused at least in part by portions of the eye (e.g., the lens of the eye) having different indexes of refraction with respect to different wavelengths of incident light. More specifically, axial (or longitudinal) chromatic aberration may cause light having different wavelengths to be focused at different depths or positions along the optical axis of the eye (e.g., in front of or behind the retina), while lateral (or transverse) chromatic aberration may cause light having different wavelengths to be focused at different lateral locations (e.g., along the retina).

While at least most types of significant monochromatic aberrations (e.g., defocus, astigmatism, spherical aberration, and the like) may vary greatly from one viewer to another, axial chromatic aberration may be relatively constant from one viewer to the next. Moreover, the amount of lateral chromatic aberration experienced by the viewer may depend on either or both the position of light in the pupil and the angle of incidence of the light when entering the eye.

SUMMARY

As will be described in greater detail below, the instant disclosure discusses systems and methods for reducing eye-related aberrations. Such systems and methods, in some examples, may be employed in a near-eye display (NED) system (e.g., a head-mounted display (HMD) or eyewear device for an augmented reality (AR), virtual reality (VR), or mixed reality (MR) system). In one example, a system may include (1) a light source that generates light for an image, (2) an optical subsystem that (a) receives the generated light from the light source, and (b) generates, based on the received light, converging light defining an exit pupil that includes the image, where the exit pupil is smaller than a pupil of an eye of a viewer, and (3) a control subsystem that controls at least one of the light source or the optical subsystem to reduce aberration of the image that is caused by the eye of the viewer. In some embodiments, the aberration may include at least one of chromatic aberration or monochromatic aberration.

In some examples, the control subsystem may control the light source to alter the light generated by the light source to modify the image to reduce the aberration. In some embodiments, the control subsystem may alter a chromatic alignment of the light generated by the light source. Additionally or alternatively, in some examples, the control subsystem may alter a geometric alignment of the light generated by the light source.

The control subsystem, in some examples, may control the optical subsystem to alter at least one of (1) a position of the exit pupil relative to the pupil of the eye of the viewer or (2) an angle of incidence of the converging light relative to the pupil of the eye of the viewer. In some embodiments, the system may further include an eye-tracking subsystem that generates tracking information indicating a gaze angle of the eye of the viewer, and the control subsystem may control the position of the exit pupil and/or the angle of incidence of the converging light based on the tracking information. Further, in some embodiments, the control subsystem may control the position of the exit pupil and/or the angle of incidence of the converging light based on a history of the tracking information to anticipate the gaze angle of the eye of the viewer. In some examples, the optical subsystem may direct the converging light along a configurable optical path between the optical subsystem and the pupil of the eye determined by the control subsystem. In such examples, (1) the control subsystem may determine (a) a direction in which the converging light is to be directed and (b) an apparent location from which the converging light is to be directed, and (2) the configurable optical path may be based at least in part on the direction and the apparent location.

In some embodiments, (1) the control subsystem may include a memory device storing configuration data indicating at least one of (a) at least one desired position of the exit pupil relative to the pupil of an eye for a plurality of viewers to reduce the aberration or (b) at least one desired angle of incidence of the converging light relative to the pupil of the eye for the plurality of viewers to reduce the aberration, and (2) the control subsystem may alter the position of the exit pupil and/or the angle of incidence of the converging light based on the configuration data. In some examples, the desired position may include a desired position for each of a plurality of aberration types, the desired angle of incidence may include a desired angle of incidence for each of the plurality of aberration types, and the control subsystem may generate at least one of a single desired position and a single desired angle of incidence based on a combination of at least one of (1) the desired position for each of the plurality of aberration types, or (2) the desired angle of incidence for each of the plurality of aberration types. In such examples, the combination may include a linear combination of a plurality of basis functions, and each of the plurality of basis functions may correspond to one of the plurality of aberration types.

In some implementations, (1) the control subsystem may include a memory device storing configuration data indicating at least one of (a) at least one desired position of the exit pupil relative to the pupil of the eye of the viewer to reduce the aberration, or (b) at least one desired angle of incidence of the converging light relative to the pupil of the eye of the viewer to reduce the aberration, and (2) the control subsystem may alter the position of the exit pupil and/or the angle of incidence of the converging light based on the configuration data. In some examples, the desired position may include a desired position for each of a plurality of aberration types, the desired angle of incidence may include a desired angle of incidence for each of the plurality of aberration types, and the control subsystem generates at least one of a single desired position and a single desired angle of incidence based on a combination of at least one of (a) the desired position for each of the plurality of aberration types, or (b) the desired angle of incidence for each of the plurality of aberration types. In such examples, the combination may include a linear combination of a plurality of basis functions, and each of the plurality of basis functions may correspond to one of the plurality of aberration types.

In one example, a method may include (1) generating, by a light source, light for an image, (2) receiving, by an optical subsystem, the generated light from the light source, (3) generating, by the optical subsystem based on the received light, converging light defining an exit pupil that includes the image, where the exit pupil is smaller than a pupil of an eye of a viewer, and (4) controlling, by a control subsystem, at least one of the light source or the optical subsystem to reduce aberration of the image that is caused by the eye of the viewer. In some embodiments, controlling the light source may include altering the light generated by the light source to modify the image to reduce the aberration. Additionally or alternatively, in some examples, controlling the optical subsystem may include altering at least one of (1) a position of the exit pupil relative to the pupil of the eye of the viewer, or (2) an angle of incidence of the converging light relative to the pupil of the eye of the viewer.

In some embodiments, a computer-readable medium may include computer-readable instructions that, when executed by at least one processor of a display device, cause the display device to (1) generate, by a light source of the display device, light for an image, (2) receive, by an optical subsystem of the display device, the generated light from the light source, (3) generate, by the optical subsystem based on the received light, converging light defining an exit pupil that includes the image, where the exit pupil is smaller than a pupil of an eye of a viewer, and (4) control at least one of the light source or the optical subsystem to reduce aberration of the image that is caused by the eye of the viewer.

Features from any of the above-mentioned embodiments may be used in combination with one another in accordance with the general principles described herein. These and other embodiments, features, and advantages will be more fully understood upon reading the following detailed description in conjunction with the accompanying appendices.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
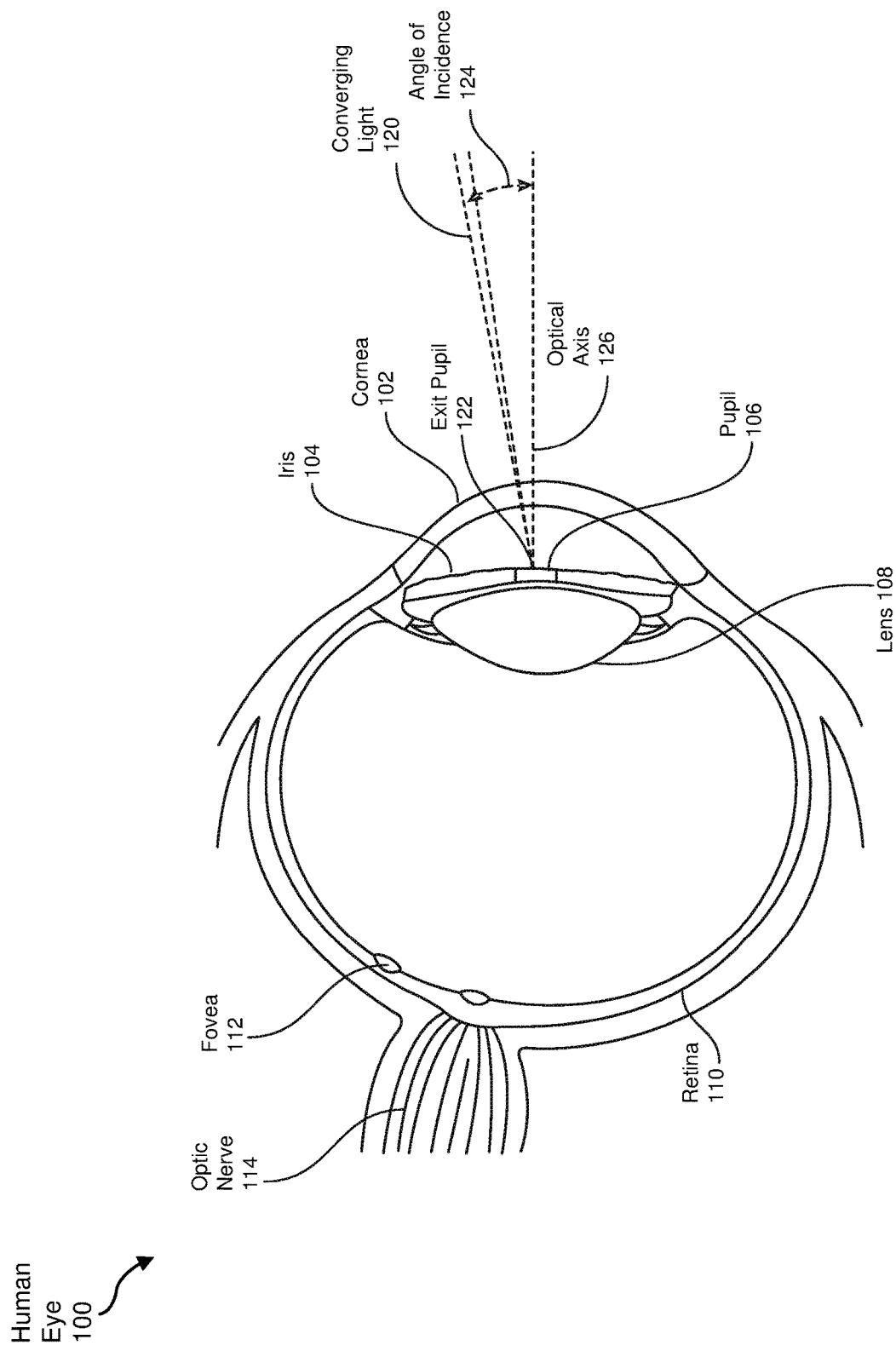
FIG. 1 is a cross-sectional view of a human eye depicting converging light that generates an exit pupil at a particular location in a pupil of the eye and enters the eye at a particular angle of incidence, as may occur in some embodiments.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to systems and methods for reduction of eye-related aberrations (e.g., monochromatic aberrations and/or chromatic aberrations). Such systems and methods, in some examples, may be employed in NEDs, such as those incorporated in VR systems, AR systems, MR systems, and the like. As will be explained in greater detail below, embodiments of the instant disclosure may facilitate greater clarity of an image being presented to the viewer by reducing (e.g., minimizing) such aberrations.

The following will provide, with reference to FIGS. 1-6, detailed descriptions of systems and methods for reducing eye-related aberrations. Directional and location control of converging light providing an exit pupil for presenting an image to a viewer to reduce eye-related aberration, as may be employed in some embodiments, is discussed in conjunction with FIG. 1. Exemplary systems for reducing eye-related aberrations are described in reference to FIGS. 2 and 3. An exemplary HMD and NED that may incorporate the disclosed systems and methods for reduction of eye-related aberrations is discussed in conjunction with FIGS. 4 and 5. In connection with FIG. 6, an exemplary method for eye-related aberration reduction is discussed.

FIG. 1 is a cross-sectional view of a human eye 100 depicting an exit pupil 122 of converging light 120 at a particular location in a pupil 106 of eye 100, and entering eye 100 at a particular angle of incidence 124 (e.g., relative to an optical axis 126 associate with eye 100), as may occur in some embodiments discussed herein. In some embodiments, exit pupil 122 may provide an image carried in converging light 120, such as what may be provided by a focusing lens (not shown in FIG. 1) or another optical element. As used herein, an exit pupil (e.g., exit pupil 122) may refer to a virtual aperture in the optical system (e.g., an NED). In some examples, light that passes through this virtual aperture may exit the optical system and enter eye 100. As indicated in FIG. 1, the size of exit pupil 122 may be less than the area of eye pupil 106 (e.g., as determined by iris 104), thus allowing exit pupil 122 to be located in a variety of locations within or on eye pupil 106 (e.g., in an x-y plane defined by eye pupil 106) while allowing the viewer to perceive a larger image (e.g., an immersive image that may include images carried via one or more exit pupils converging on different locations within or on eye pupil 106 or a real-life image being transmitted to eye 100 through a lens (e.g., a lens in an AR or MR display)). In other examples, a center of exit pupil 122 may be offset from a center of eye pupil 106. In some examples, exit pupil 122 may be larger than eye pupil 106, which may result in a corresponding region of overlap between exit pupil 122 and eye pupil 106. Further, in such embodiments, the center of exit pupil 122 may or may not be concentric with the center of eye pupil 106.

In some examples, the amount of optical aberration (e.g., chromatic and/or monochromatic aberration) generated by eye 100 (e.g., by way of a shape (e.g., oblateness, prolateness, and so on) or an optical characteristic (e.g., index of refraction, transparency, etc.) of cornea 102, lens 108, and/or other portions of eye 100) may vary depending on the current location of exit pupil 122 and/or angle of incidence 124 of converging light 120 (e.g., angle of incidence 124 of converging light 120 at cornea 102). Consequently, a particular location of exit pupil 122 and/or angle of incidence 124 of converging light 120 may correspond to a reduced (e.g., minimal) level of at least one particular type of aberration (e.g. a dominant aberration, such as axial or lateral chromatic aberration). In some embodiments, differences in the amount of one or more types of aberration relative to a particular location of exit pupil 122 and/or angle of incidence 124 of converging light 120 may be similar, or substantially the same, from person to person (e.g., for some types of monochromatic aberration), and/or may be substantially different from person to person (e.g., for some higher-order aberrations), and may depend on the type of aberration (e.g., monochromatic or chromatic aberration). In some examples, the amount of one or more types of aberration may be influenced by the size of exit pupil 122, the size of eye pupil 106, and/or the size of exit pupil 122 relative to eye pupil 106. For example, larger eye pupil 106 sizes may generally lead to a greater portion of an optical waveform (e.g., a wave of incident light 120 having a constant phase, discussed in greater detail below) to pass through lens 108 and/or other portions of eye 100, thereby possibly leading to increases in optical aberrations, particularly in low lighting conditions when eye pupil 106 is larger.

While FIG. 1 depicts angle of incidence 124 as being vertically oriented relative to human eye 100, other angles of incidence 124 in other directions (e.g., horizontal, out-of-plane, and/or combinations thereof) about optical axis 126 through eye pupil 106 are also possible. In some examples, the location of exit pupil 122 and/or angle of incidence 124 may be set to cause the image of converging light 120 to focus on the fovea 112 (e.g., the region of eye 100 where the center of the field-of-vision may be focused and where retinal cones are particularly concentrated) of the retina 110, near the entry point of optic nerve 114, which may be considered the portion of retina 110 that provides the highest resolution.

Figure 2:
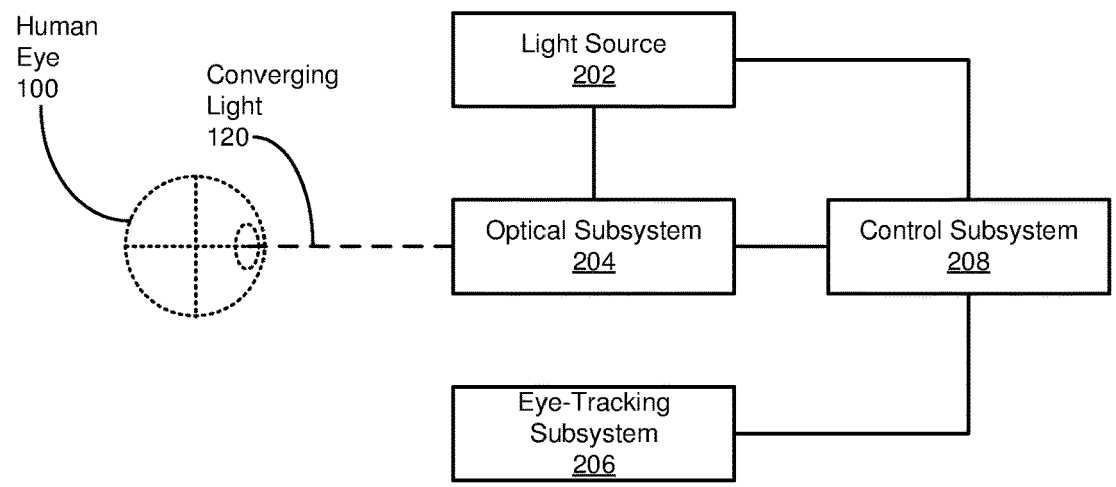
FIG. 2 is a block diagram of an exemplary display system for reducing eye-related aberrations.

FIG. 2 is a block diagram of an exemplary display system 200 for reducing eye-related aberrations. As depicted in FIG. 2, display system 200 may include a light source 202, an optical subsystem 204, an eye-tracking subsystem 206, and/or a control subsystem 208. In some embodiments, light source 202 may generate light for an image (e.g., to be presented to eye 100 of the viewer). Light source 202, in some embodiments, may include any of a variety of suitable devices. For example, light source 202 can include a two-dimensional projector (e.g., a liquid-crystal-on-silicon (LCoS) display), a scanning source (e.g., a scanning laser), or other device (e.g., a liquid crystal display (LCD), a light-emitting diode (LED) display, an organic light-emitting diode (OLED) display, an active-matrix OLED display (AMOLED), a transparent OLED display (TOLED), or some other display) capable of generating light for presenting an image to the viewer. In some examples, the image may include a virtual image, which may refer to an optical image formed from the apparent divergence of light rays from a point in space, as opposed to an image formed from their actual divergence.

Optical subsystem 204, in some embodiments, may receive the generated light from light source 202 and generate, based on the received light, converging light 120 exit pupil 122 that includes the image, where exit pupil 122 may be smaller than pupil 106 of eye 100. For example, exit pupil 122 may encompass a smaller surface area (e.g., approximately one-fifth the surface area) of eye pupil 106. In some examples, optical subsystem 204 may include any number of lenses (e.g., a Fresnel lens, a convex lens, a concave lens, and so on), apertures, filters, mirrors, prisms, and/or other optical components, possibly in combination with one or more actuators or other devices that translate and/or rotate one or more of the optical components to alter one or more aspects of converging light 120, as well as mechanical couplings to maintain relative spacing and orientation of one or more of the optical components in a combination. Further, one or more of the optical components may have an optical coating, such as an anti-reflective coating, or a combination of optical coatings. In some embodiments, optical subsystem 204 may alter one or more of a position of exit pupil 122 relative to eye pupil 106, and/or angle of incidence 124 of converging light 120 relative to eye pupil 106. In some embodiments, optical subsystem 204 may direct converging light 120 along a configurable optical path (e.g., determined by control subsystem 208) between optical subsystem 204 and eye pupil 106.

For example, optical subsystem 204 can direct converging light 120 through one or more optical elements (e.g., lenses, prisms, waveguides, and the like) in a folded optical path before reaching the eye pupil 106. In some embodiments, optical subsystem 204 may modify the size (e.g., the radius) of exit pupil 122. For example, optical subsystem 204 increase or decrease the size of exit pupil 122, for example, to reduce one or more optical aberrations (e.g., one or more dominant optical aberrations) associated with eye 100. In some examples, optical subsystem 204 can use an exit pupil expander or an exit pupil contractor (not shown in FIG. 2) to change the size of exit pupil 122. In some examples, the exit pupil expander or the exit pupil contractor may include one or more of a diffuser (e.g., a micro-lens or micro-lens array) and one or more optical elements making up a lens assembly. The lens assembly may include an input end for receiving output light emerging from diffuser (e.g., for the exit pupil expander), an output end forming a second exit pupil having a modified exit pupil size, and one or more optical lenses positioned between the input end and the output end. In one embodiment, the lenses may be aspherical or free-form lenses made of plastic, which may significantly reduce the overall size, weight, and cost of the lens assembly. In some embodiments, the expansion or contraction of the size of exit pupil 122 may be optimized for optical element properties (e.g., a projecting lens numerical aperture) used by optical subsystem 204 in generating or modifying converging light 120.

Additionally or alternatively, in some examples, optical subsystem 204 may facilitate the alteration of a geometric alignment and/or a chromatic property or alignment (e.g., a center wavelength, an intensity, a polarization, and the like) of the light received from light source 202, such as by way of translation and/or rotation of one or more lenses (e.g., a Fresnel lens, a convex lens, a concave lens, and the like), prisms, diffusers, apertures, filters, polarizers, mirrors, and the like, to minimize the resulting image aberrations caused by eye 100. In some embodiments, optical subsystem 204 may be designed to correct one or more types of optical error, such as two-dimensional optical errors, three-dimensional optical errors, or a combination thereof. Two-dimensional errors are optical aberrations that occur in two dimensions. Example types of two-dimensional errors may include barrel distortion, pincushion distortion, longitudinal chromatic aberration, and transverse chromatic aberration. Three-dimensional errors are optical errors that occur in three dimensions. Example types of three-dimensional error may include spherical aberration, chromatic aberration, field curvature, and astigmatism.

Eye-tracking subsystem 206, in some embodiments, may generate tracking information indicating a gaze angle of eye 100 of the viewer. As used herein, eye-tracking may refer to a process by which the position, orientation, and/or motion of the eye 100 may be measured, detected, sensed, determined, and/or monitored. The position, orientation, and/or motion of the eye 100 may be measured in a variety of ways, such as by using one or more sensors to optically track the eye. Control subsystem 208, in some examples, may control optical subsystem 204 (e.g., at least one of the position of exit pupil 122 or angle of incidence 124 of converging light 120) based at least in part on the tracking information. Additionally, in some examples, control subsystem 208 may employ a history of the tracking information (e.g., over a given duration such as the previous second or fraction thereof) to anticipate the gaze angle of eye 100 (e.g., an angle between the visual axis and the anatomical axis of eye 100). In some embodiments, eye-tracking subsystem 206 may employ infrared (IR) or near-infrared (NIR) light to detect radiation emanating from a portion of eye 100 (e.g., cornea 102, iris 104, pupil 106, or the like) to determine the current gaze angle of eye 100. In other examples, eye-tracking subsystem 206 may employ a wavefront sensor to track the current location of pupil 106.

Any number of techniques may be used to track eye 100. Some techniques may involve illuminating eye 100 with infrared light and measuring reflections with at least one optical sensor that is tuned to be sensitive to the infrared light. Information about how the infrared light is reflected from eye 100 may be analyzed to determine the position, orientation, and/or motion of one or more eye features, such as cornea 102, iris 104, pupil 106, and/or retinal blood vessels.

In some examples, the radiation captured by a sensor used in eye-tracking may be digitized (e.g., converted to an electronic signal by the sensor). Further, a digital representation of this electronic signal may be transmitted to one or more processors (for example, processors associated with a device including eye-tracking subsystem 206).

In some embodiments, the sensors of the eye-tracking subsystem 206 may include any suitable configuration and may include a variety of types. For example, the sensor may include an infrared detector that reacts to infrared radiation. The infrared detector may be a thermal detector, a photonic detector, and/or any other suitable type of detector. Thermal detectors may include detectors that react to thermal effects of the incident infrared radiation. For example, bolometers may be examples of thermal detectors that may have a change in resistance based on infrared radiation and may be used as a sensor. Additional examples that may be used as the sensor may include, but are not limited to, thermocouples and thermopiles, which may respond to a thermoelectric effect. Another example of sensor may include a Golay cell that detects incident infrared radiation based on a thermal expansion effect.

In some examples, the digital representation generated by the sensors of eye-tracking subsystem 206 may be processed by the one or more processors to track the movement of eye 100. In some embodiments, the tracking of the movements of eye 100 may be performed by executing, by the one or more processors, one or more algorithms represented by computer instructions stored on non-transient memory. In some examples, at least portions of such algorithms may be performed using on-chip logic (e.g., an application-specific integrated circuit (ASIC)).

As noted, eye-tracking subsystem 206 may be programmed to use an output of the sensors to track movement of eye 100. In some embodiments, the digital representation generated by the sensors may be analyzed by eye-tracking subsystem 206 to extract eye rotation from changes in reflections. In one embodiment, corneal reflection (which may be referred to as a first Purkinje image) and/or a center of the eye pupil 106 may be used as features to track over time. In another embodiment, a dual-Purkinje eye-tracking process may be implemented, which uses reflections from the front of cornea 102 (first Purkinje image) and the back of lens 108 (fourth Purkinje image) as features to track. In another embodiment, image features from inside eye 100, such as the retinal blood vessels, may be imaged and tracked as the eye rotates. Purkinje images may refer to reflections of objects from the structure of eye 100. They may also be referred to as Purkinje reflexes and Purkinje-Sanson images. The first Purkinje image may refer to the reflection from the outer surface of cornea 102. The second Purkinje image may refer to the reflection from the inner surface of the cornea. The third Purkinje image may refer to the reflection from the outer (anterior) surface of lens 108 of eye 100. The fourth Purkinje image may refer to the reflection from the inner (posterior) surface of lens 108 of eye 100.

In some embodiments, eye-tracking subsystem 206 may use the center of eye pupil 106 and infrared or near-infrared, non-collimated light to create corneal reflections. The vector between the center of eye pupil 106 and the corneal reflections may be used to compute the gaze direction of eye 100. In some embodiments, a calibration procedure of the individual, for example, a calibration procedure to determine the vector mentioned above, may be performed before eye-tracking.

In some embodiments, eye-tracking subsystem 206 may use two types of infrared and/or near-infrared (also known as active light) eye-tracking techniques: bright-pupil eye-tracking and dark-pupil eye-tracking, which may be differentiated based on the location of an illumination source with respect to the optics. If the illumination is coaxial with the optical path, then eye 100 may act as a retroreflector as the light reflects off the retina, thereby creating a bright pupil effect similar to red eye. If the illumination source is offset from the optical path, then eye pupil 106 may appear dark because the retroreflection from the retina is directed away from the sensor. In some embodiments, bright-pupil tracking may create greater iris/pupil contrast, allowing more robust eye-tracking with iris pigmentation, and with reduced interference that may be caused by eyelashes and other obscuring features. Also, in some examples, bright-pupil tracking may also allow tracking in lighting conditions ranging from total darkness to very bright.

Control subsystem 208, in some embodiments, may control one or more of light source 202 and optical subsystem 204 to reduce optical aberrations (e.g., chromatic aberrations and/or monochromatic aberrations) of the image that may be caused or influenced by eye 100 of the viewer. In some examples, as mentioned above, control system 208 may use the tracking information from eye-tracking subsystem 206 to perform such control. For example, in controlling light source 202, control subsystem 208 may alter the light generated by light source 202 (e.g., by way of image rendering) to modify (e.g., pre-distort) the image so that the aberration of the image caused by eye 100 is reduced. Such alterations may include, but not limited to, alterations of the chromatic alignment and/or geometric alignment of the light. In some examples, altering the chromatic alignment (e.g., the spatial alignment of the red, green, and blue portions of the light) by control subsystem 208 may correct for one or more chromatic aberrations of eye 100, thereby possibly resulting in a more accurate chromatic alignment of the colors of the original or intended image at retina 110. In some embodiments, altering the geometric alignment (e.g., locations within the image for various portions of the image, such as dots, lines, etc.) by control subsystem 208 may correct for one or more monochromatic aberrations of eye 100, possibly resulting in a more accurate geometric alignment of the original or intended image at retina 110.

In some examples, multiple pupil replications may be generated by control subsystem 208 and optical subsystem 204 at the exit pupil (e.g., exit pupil 122) for different colors of light. For example, multiple exit pupils may be used to create a larger effective eyebox (e.g., an optical measurement usually expressed in millimeters that characterizes how much the eye 100 can move from an optimal position without degradation in the quality of the viewed image) for eye 100, and can allow for large field-of-view images to be scanned by eye 100. In some embodiments, the individual eyeboxes associated with each exit pupil 122 location may overlap one another so that the overall effective eyebox can be made continuous (e.g., without gaps in the viewable image space of eye 100). In some examples, an array of exit pupils 122 may be generated by using control subsystem 208 and optical subsystem 204, such that the field-of-view of eye 100 intersects one or more of the exit pupils. The array may have any suitable shape, e.g., rectangular, triangular, circular, and the like, and may be periodic, semi-periodic, or aperiodic (e.g., non-uniform), for example, to reduce one or more types of optical aberrations (e.g., dominant aberrations) of the eye 100.

In some embodiments, different center wavelengths of light (e.g., based on different sub-pixels or light beams from light source 202) may be used by control subsystem 208 and optical subsystem 204 to produce multiple independent exit pupils (e.g., without significant crosstalk). In some example, multiple exit pupils may be generated for one color-type having separated wavelengths. For example, one or more exit pupil 122 locations may be generated using several different green light sources with different center wavelengths. Accordingly, incident light on a particular position on eye 100 may appear on retina 110 at different positions for the different center wavelengths, which can correspond to different angular content of the light of the different exit pupils 122. In some embodiments, a full-color exit pupil 122 can be generated by spacing red, green, and blue (RGB) light (e.g., from different subpixels or light beams of the light source 202) accordingly for each exit pupil 122 location.

In controlling optical subsystem 204, control subsystem 208, in some embodiments, may determine an optical path (e.g., the path that light takes in traversing an optical medium or system) between optical subsystem 204 and eye pupil 106 along which optical subsystem 204 may direct converging light 120. In some examples, control subsystem 208 may determine a direction from optical subsystem 204 in which converging light 120 is to be directed, and an apparent or actual location on or in optical subsystem 204 from which converging light 120 is to be directed. Based on the direction and apparent or actual location of the converging light 120, control subsystem 208 may determine one or more optical paths to direct converging light 120. Additionally or alternatively, control subsystem 208 may control optical subsystem 204 to facilitate the alteration of the geometric alignment and/or the chromatic properties and/or alignment of the light received from light source 202 and present in converging light 120. In some embodiments, control subsystem 208 may make these determinations and/or alterations based on various factors, such as a determined location for exit pupil 122 and/or an angle of incidence 124 of converging light 120, that may reduce (e.g., minimize) one or more aberrations cause by eye 100. Moreover, as described above, control subsystem 208 may further determine the direction and location of converging light 120, and/or alter the light received from light source 202, in view of a current gaze angle of eye 100, as indicated in the tracking information received from eye-tracking subsystem 206.

In some embodiments, control subsystem 208 may also include a memory device (not illustrated in FIG. 2) that may store configuration data indicating a determined position of exit pupil 122 relative to eye pupil 106 and/or a determined angle of incidence 124 of converging light 120 to reduce at least one type of aberration (e.g., monochromatic or chromatic aberration) associated with eye 100. Control subsystem 208 may employ the configuration data to control optical subsystem 204 (e.g., in conjunction with the tracking information from eye-tracking subsystem 206) to reduce (e.g., minimize) aberrations of the image presented to eye 100. In some examples, multiple values including desired positions of exit pupil 122, sizes of exit pupil 122 (e.g., with respect to a size of eye pupil 106) and/or multiple desired angles of incidence 124 may be stored in the memory device, where each of the multiple values may be associated with a particular aberration type. In such an example, control subsystem 208 may combine some plurality of the locations of exit pupil 122 and/or angles of incidence 124 (e.g., by a linear combination of basis functions, where the basis functions correspond to the aberration types (e.g., chromatic aberration, monochromatic aberration, astigmatism, spherical aberration, and the like). An example set of basis functions that can be used includes Zernike polynomials, which can refer to a sequence of polynomials that are orthogonal on the unit disk. For example, a number of Zernike polynomials (e.g., the first 15. Zernike polynomials) may be used to determine an accurate characterization of the most common aberrations of the eye.

In other embodiments, each of the plurality of locations of exit pupil 122 and/or angles of incidence 124 of converging light 120 may correspond to a local minimum of a given optical aberration. Accordingly, control subsystem 208 may select a closest location and/or an optimized angle of incidence 124 of the plurality of locations of exit pupil 122 and/or angles of incidence 124 of converging light 120 relative to a current location of exit pupil 122 and/or angle of incidence 124 of converging light 120 (e.g., as indicated by eye-tracking subsystem 206). In some examples, the configuration data may be stored in the memory device as one or more lookup tables or other data structures, and may be applicable to individual viewers (e.g., where the memory device stores separate information for each individual viewer), to a group of viewers of a given type (e.g., classified by gender, age, height, or any other suitable feature), or to viewers in general. As noted above, in some embodiments, the configuration data may be generally applicable to all viewers (e.g., in cases in which minimal variations in the configuration data exist between individual viewers of the general population). In other examples (e.g., in which the configuration data may vary greatly from one viewer to the next), an external optical testing system (e.g., a diagnostic imaging system for testing retina 110 or cornea 102 of human eye 100, such as with an adaptive optics scanning laser ophthalmoscopy (AOSLO) system) may be employed to determine optical aberrations (e.g., chromatic and/or monochromatic aberrations) associated with each individual viewer for a variety of locations of exit pupil 122 and/or angles of incidence 124 of converging light 120, with the configuration data stored in the memory device being based on those determinations. In particular examples, the AOSLO system may be used to determine the lateral (transverse) chromatic aberrations.

In yet other embodiments, a wavefront sensor or other optical device capable of detecting one or more aspects of the optical aberrations associated with eye 100 of a current viewer may be employed within display system 200 to populate the configuration data in the memory device for the current viewer. In some examples, a wavefront sensor may refer to a device for measuring the aberrations of an optical wavefront. A uniform wavefront of light rays passing through an eye 100 acquires certain three-dimensional, distorted shapes referred to as a wavefront. In one aspect, an optical wavefront can refer to a surface of an optical light wave over which the wave has a constant phase. In some examples, for light to converge to a single point in the eye 100, an ideal wavefront passing through the eye 100 may need to have a particular shape (e.g., a hemispherical shape), which may need to be centered on the image point within eye 100 (e.g., on retina 110). The difference between an actual wavefront of light passing through eye 100 and the ideal wavefront can be referred to as the wavefront aberration of eye 100. As noted, one or more optical aberration associated with eye 100 of a current viewer may be characterized using the wavefront sensor, for example, to populate configuration data in the memory device for the current viewer.

In some embodiments, various types of wavefront sensors and associated techniques may be used to determine the optical aberrations of eye 100 based on wavefront characterization. Non-limiting examples may include a Shack-Hartmann wavefront sensor, a phase-shifting Schlieren technique, a wavefront curvature sensor, a pyramid wavefront sensor, a common path interferometer, a Foucault knife-edge test, a multilateral shearing interferometer, and/or a Ronchi tester. In some examples, algorithmic techniques (e.g., phase imaging or curvature sensing) may determine wavefronts from brightfield images (e.g., where images of eye 100 are dark and contrasted by a surrounding bright viewing field) at different focal planes without the need for specialized wavefront optics. More than 60 different wavefront shapes or aberrations have been identified through various techniques, such as those mentioned above, and a portion of those aberrations can be reduced by the systems, methods, and apparatuses described herein.

As noted above, the configuration data may be stored in the memory device as one or more lookup tables or other data structures. In some examples, the configuration data may be stored on a cloud computing environment and may be periodically updated with modified or additional configuration data from users. This configuration data can be used by control subsystem 208 to select the closest location and/or an optimized angle of incidence 124 of the plurality of locations of exit pupil 122 and/or angles of incidence 124 of converging light 120 relative to a current location of exit pupil 122 and/or angle of incidence 124 of converging light 120.

As mentioned, the configuration data can be hosted on a cloud computing platform. Further, one or more databases can be used to store and modify the configuration data and can be stored or hosted on a cloud computing platform. Further, implementation of the teachings recited herein are not limited to a cloud computing environment. Rather, embodiments of the present invention are capable of being implemented in conjunction with any other type of computing environment now known or later developed.

As used herein, cloud computing may refer to a model of service delivery for enabling convenient, on-demand network access to a shared pool of configurable computing resources (e.g., networks, network bandwidth, servers, processing, memory, storage, applications, virtual machines, and services) that may be rapidly provisioned and released with minimal management effort or interaction with a provider of the service. As shown, a cloud computing environment may include one or more cloud computing nodes with which local computing devices used by cloud consumers, such as, for example, personal digital assistants (PDAs) or cellular telephones, desktop computers, laptop computers, and/or automobile computer systems, and the like, can communicate. The nodes may communicate with one another. Also, the nodes may be grouped physically or virtually, in one or more networks, such as private, community, public, or hybrid clouds. These characteristics may allow a cloud computing environment to offer infrastructure, platforms, and/or software as services for which a cloud consumer does not need to maintain resources on a local computing device. In various aspects, a cloud computing environment may communicate with any type of computerized device over any type of network and/or network addressable connection (e.g., using a web browser).

Figure 3:
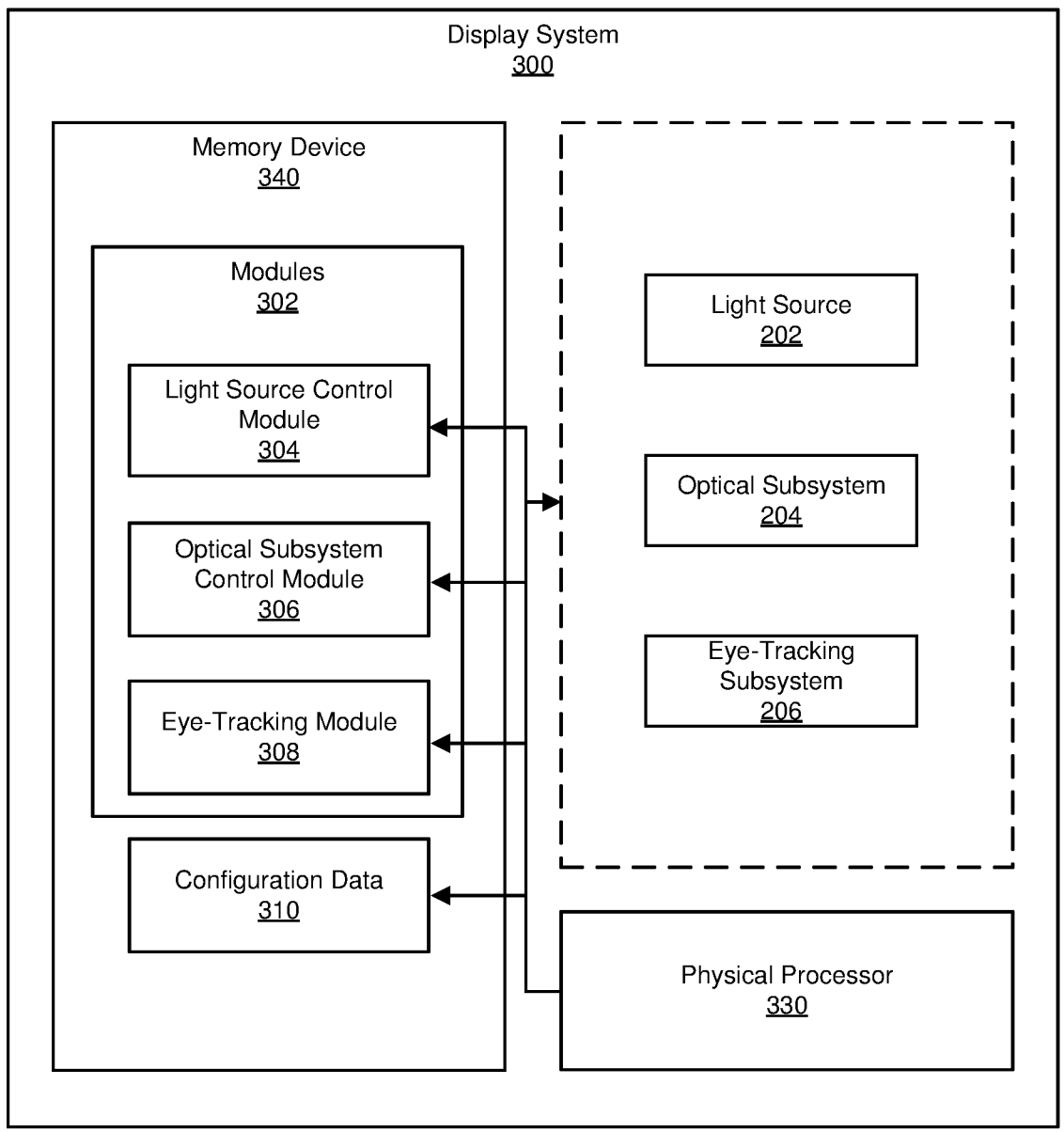
FIG. 3 is a block diagram of another exemplary display system for reducing eye-related aberrations.

FIG. 3 is a block diagram of another exemplary display system 300 for reducing eye-related optical aberrations (e.g., chromatic or monochromatic aberrations). As illustrated in FIG. 3, display system 300 may include one or more modules 302 for performing one or more tasks. As will be explained in greater detail below, modules 302 may include a light source control module 304, an optical subsystem control module 306, and an eye-tracking module 308. Although illustrated as separate elements, one or more of modules 302 in FIG. 3 may represent portions of a single module or application. In at least some embodiments, display system 300 may also include light source 202, optical subsystem 204, and/or eye-tracking subsystem 206, examples of which are described in greater detail above.

Light source control module 304, in some examples, controls the output of light source 202. In some embodiments, light source control module 304 may alter an input signal provided to light source 202, such as by altering a chromatic property or alignment and/or a geometric alignment of the input signal, as described above, to at least partially counteract the effects of eye-related aberrations (e.g., chromatic and/or monochromatic aberrations), as discussed above. In some examples, light source control module 304 may base such alterations at least in part on tracking information received from eye-tracking subsystem 206.

Optical subsystem control module 306, in some embodiments, may communicate with optical subsystem 204 to control the current location for exit pupil 122 and/or the current angle of incidence 124 of converging light 120 into human pupil 106, as described above. In some examples, optical subsystem control module 306 may base its control of optical subsystem 204 on tracking information received from eye-tracking subsystem 206, as well as on configuration data 310, according to the above disclosure. As discussed above, configuration data 310, in some embodiments, may include one or more locations for exit pupil 122 and/or angles of incidence 124 resulting in a reduction (e.g., minimization) of eye-related optical aberrations, as discussed above. Additional or alternatively, optical subsystem control module 306, in some examples, may alter a chromatic property or alignment and/or a geometric alignment within converging light 120, for example, based on the tracking information received from eye-tracking subsystem 206 and/or configuration data 310.

Eye-tracking module 308, in some examples, may receive tracking information from eye-tracking subsystem 206 indicative of the current gaze angle of eye 100. In some embodiments, eye-tracking module 308 may also store a history of gaze angles of eye 100, and may use the history of the gaze angles of eye 100 to generate a predicted or anticipated future gaze angle of eye 100, which either or both of light source control module 304 or optical subsystem control module 306 may use to perform their associated alteration tasks. In some examples, data corresponding to the history of the gaze angles of eye 100 may be used in connection with a time-series model based on artificial intelligence (AI) to determine the predicted or anticipated future gaze angle of eye 100. For example, the data corresponding to the history of the gaze angles of eye 100 may be used in connection with a neural network model. In some embodiments, the neural network may include a recurrent neural network (RNN). In some examples, time-domain methods, such as auto-correlation and cross-correlation analysis, may be used, including parametric and non-parametric methods. The parametric approaches may assume that the underlying stationary stochastic of process corresponding to the gaze angles of eye 100 has a certain structure which can be described using a small number of parameters (for example, using an autoregressive or moving average model). In these approaches, the time-domain methods may estimate the parameters of the model that describe the stochastic process associated with the gaze angles of eye 100.

As noted, eye-tracking module 308 may employ AI to facilitate automating one or more features described herein. The components may employ various AI-based schemes for carrying out various embodiments/examples disclosed herein, for example, related to the tracking of the gaze angles of the eye 100. To provide for or aid in the numerous determinations (e.g., determine, ascertain, infer, calculate, predict, prognosticate, estimate, derive, forecast, detect, compute) described herein, components described herein may examine the entirety or a subset of the data to which it is granted access corresponding to the gaze angles of eye 100 and can provide reasoning about, or determine states of, the system, environment, etc. from a set of observations as captured via events and/or data corresponding to the gaze angles of eye 100. Determinations can be employed to identify a specific context or action, or can generate a probability distribution over states, for example. The determinations may be probabilistic; in other words, the computation may provide a probability distribution over states of interest based on a consideration of data and events. Determinations may also refer to techniques employed for composing higher-level events from a set of events and/or data.

Such determinations may result in the construction of new events or actions (e.g., anticipated gaze angles of eye 100) from a set of observed events and/or stored event data (e.g., corresponding to the gaze angles of eye 100), whether the events are correlated in close temporal proximity, and whether the events and data come from one or several event and data sources. Components disclosed herein may employ various classification (e.g., explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined actions in connection with the claimed subject matter. Thus, classification schemes and/or systems may be used to automatically learn and perform a number of functions, actions, and/or determinations.

In certain embodiments, one or more of modules 302 in FIG. 3 may represent one or more software applications or programs that, when executed by a computing device, may cause the computing device to perform one or more tasks. One or more of modules 302 in FIG. 3 may also represent all or portions of one or more special-purpose computers configured to perform one or more tasks.

As illustrated in FIG. 3, display system 300 may also include one or more memory devices, such as memory device 340. Memory device 340 generally represents any type or form of volatile or non-volatile storage device or medium capable of storing data and/or computer-readable instructions. In one example, memory device 340 may store, load, and/or maintain one or more of modules 302. As illustrated in FIG. 3, display system 300 may also include one or more physical processors, such as physical processor 330, that may access and/or modify one or more of modules 302 stored in memory device 340, thus operating as control subsystem 208 of FIG. 2. Additionally or alternatively, physical processor 330 may execute one or more of modules 302. In yet other examples, one or more of modules 302, or portions thereof, instead may be implemented as hardware components not stored in memory device 340, such as electronic circuitry for performing one or more tasks described above. Additionally, in some examples, memory device 340 may include information generated and/or employed by modules 302, as described above, such as configuration data 310.

In other examples, some functionality described above as performed by physical processor 330 executing modules 302 may instead be performed by special-purpose circuitry included in display system 300.

Figure 4:
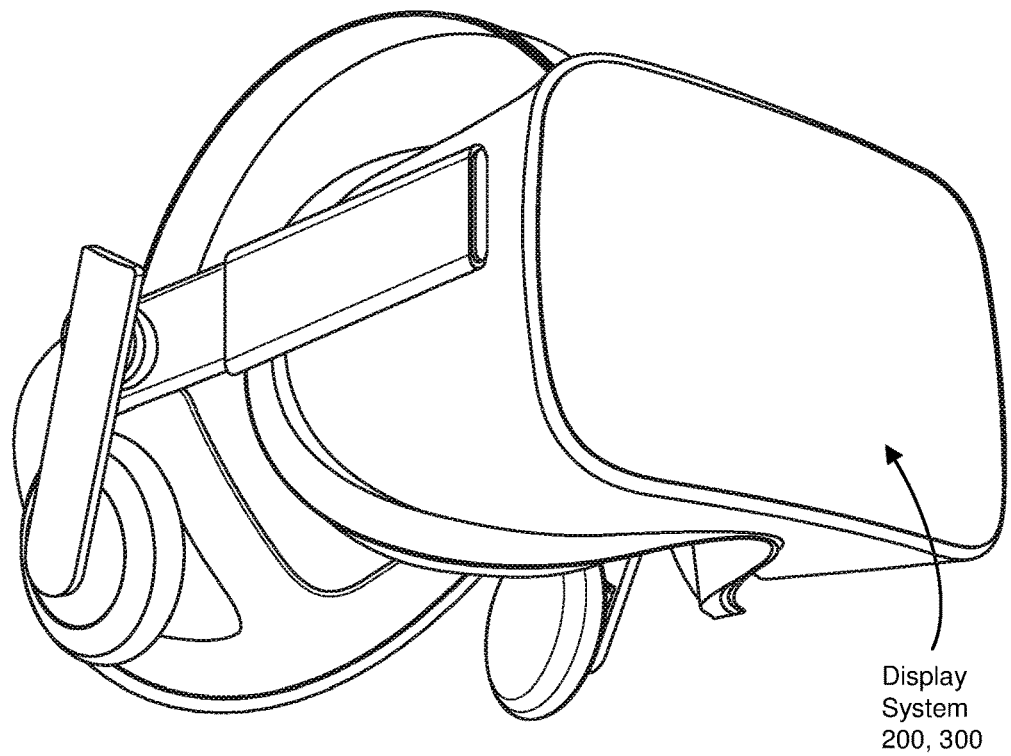
FIG. 4 is a perspective view of an exemplary HMD in which the exemplary display systems of FIGS. 2 and 3 may be employed.

FIG. 4 is a perspective view of an exemplary HMD 400 that may present images to the eyes (e.g., eye 100) of a viewer as part of a VR, AR, or MR system. To present these images, HMD 400, in some embodiments, may include at least one exemplary display system 200 or 300 that may reduce eye-related aberrations. In some embodiments, two separate display systems 200 or 300, one per viewer eye 100, may be incorporated in HMD 400. In various embodiments, display system 200 or 300 may include a light source, various possible types of which are mentioned above. Display system 200 or 300 may include sub-pixels to emit light of a predominant color such as red, green, blue, white, or yellow. In some embodiments, display system 200 or 300 may render display frames using a display driver that supplies display data to pixels arranged in rows controlled by a gate driver. Display system 200 or 300 may display a three-dimensional (3D) image through stereo effects produced by two-dimensional (2D) panels to create a subjective perception of image depth. For example, display system 200 or 300 may include a left display and a right display positioned in front of a user's left eye and right eye, respectively. In some examples, the left and right displays may present copies of an image shifted horizontally relative to each other to create a stereoscopic effect (e.g., a perception of image depth by a user viewing the image).

Figure 5:
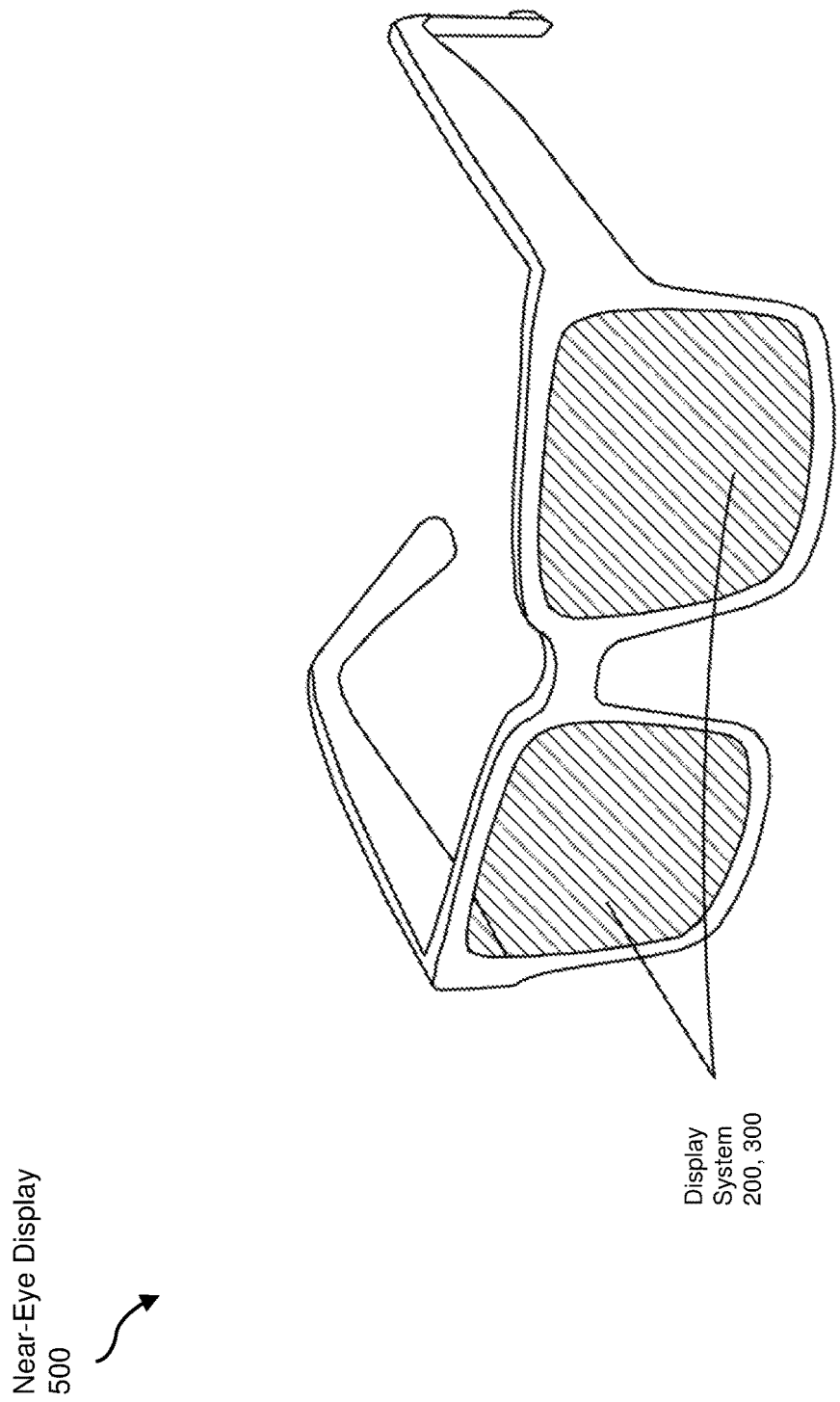
FIG. 5 is a perspective view of an exemplary NED in which the exemplary display systems of FIGS. 2 and 3 may be employed.

FIG. 5 is a perspective view of an exemplary NED 500 that may present images to the eyes (e.g., eye 100) of a viewer as part of a VR, AR, or MR system. To present these images, NED 500, in some embodiments, may include at least one exemplary display system 200 or 300 that may reduce eye-related aberrations. In some embodiments, two separate display systems 200 or 300, one per viewer eye 100, may be incorporated in NED 500.

Figure 6:
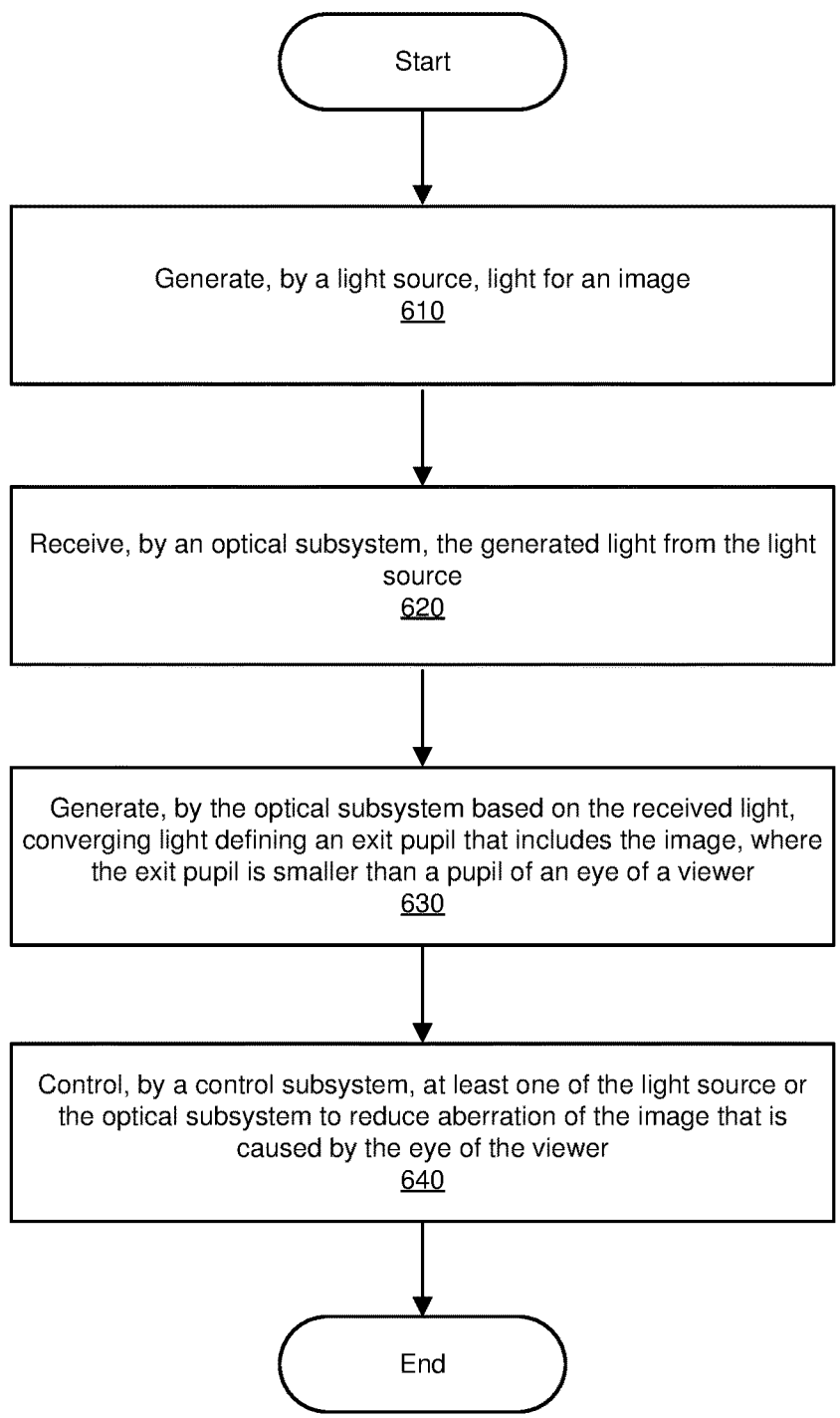
FIG. 6 is a flow diagram of an exemplary method of reducing eye-related aberrations.

FIG. 6 is a flow diagram of an exemplary method 600 of reducing eye-related aberrations. The steps shown in FIG. 6 may be performed by any suitable computer-executable code and/or computing system, including the systems illustrated in FIGS. 2 and 3. In one example, each of the steps shown in FIG. 6 may represent an algorithm whose structure includes and/or is represented by multiple sub-steps, examples of which are described above in greater detail.

As illustrated in FIG. 6, at step 610, a light source (e.g., light source 202) may generate light for an image, such as an image to be seen by a viewer (e.g., a user of HMD 400 or NED 500). At step 620, an optical subsystem (e.g., optical subsystem 204) may receive the generated light from the light source. Further, at step 630, the optical subsystem, based on the received light, may generate converging light defining an exit pupil (e.g., exit pupil 122) that includes the image, where the exit pupil is smaller (e.g., has a smaller surface area) than a pupil of an eye of a viewer. At step 640, a control subsystem (e.g., control subsystem 208, possibly as implemented as modules 302 of FIG. 3) may control at least a property of at least one of the light source or the optical subsystem to reduce optical aberrations of the image that may be caused or influenced by the eye of the viewer, such as described above.

As explained above in conjunction with FIGS. 1 through 6, the systems and methods described herein may facilitate a reduction of eye-related optical aberrations produced in images seen by a viewer, such as a user of an NED, for example. In some embodiments, a controllable optical system may be employed to alter a location of an exit pupil and/or an angle of incidence at which converged light produced by a display system enters the eye of the viewer, wherein the chosen location of the exit pupil and/or the angle of incidence of the converged light may be associated with a reduced (e.g., minimized) level of optical aberration for the user (e.g., based on prior testing of the viewer or a group of viewers). In other examples, the light source producing the image may alter the image prior to presentation to the viewer to compensate for the aberrations cause by the structure of the human eye. Either or both types of alterations may be employed to reduce one or more types of eye-related aberrations. Since the magnitude of some types of these aberrations may depend on the location and/or angle of incidence of the light as it enters the eye, eye-tracking functionality may be employed to determine a current gaze angle and/or previous gaze angles of the eye of the viewer so that one or more of the properties of the light being generated or parameters associated with the optical subsystem used to deliver the light to the eye of the viewer may be altered while taking the current gaze angle and/or previous gaze angles into account.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive data indicating desired exit pupil locations and/or angles of incidence, as well as a current gaze angle of the viewer, and then employ that data to generate control data for a light source and/or an associated optical subsystem to reduce eye-related aberrations of images being displayed to a user. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A system comprising:
    a light source that generates light for an image;
    an optical subsystem that:
        receives the generated light from the light source; and
        generates, based on the received light, converging light defining an exit pupil that includes the image; and
    a control subsystem that:
        comprises a memory device storing configuration data, wherein the configuration data indicates at least one of:
            at least one desired position of the exit pupil relative to a pupil of an eye of a viewer to reduce aberration of the image that is caused by the eye of the viewer; or
            at least one desired angle of incidence of the converging light relative to the pupil of the eye of the viewer to reduce the aberration; and
        controls at least one of the light source or the optical subsystem to reduce the aberration by altering, based on the configuration data, at least one of:
            a position of the exit pupil relative to the pupil of the eye of the viewer; or
            an angle of incidence of the converging light relative to the pupil of the eye of the viewer.

2. The system of claim 1, wherein the aberration comprises at least one of:
    chromatic aberration; or
    monochromatic aberration.

3. The system of claim 1, wherein the control subsystem controls the light source to alter the light generated by the light source to modify the image to reduce the aberration.

4. The system of claim 3, wherein the control subsystem alters a chromatic alignment of the light generated by the light source.

5. The system of claim 3, wherein the control subsystem alters a geometric alignment of the light generated by the light source.

6. The system of claim 1, wherein:
    the system further comprises an eye-tracking subsystem that generates tracking information indicating a gaze angle of the eye of the viewer; and
    the control subsystem controls the at least one of the position of the exit pupil or the angle of incidence of the converging light based at least in part on the tracking information.

7. The system of claim 6, wherein the control subsystem controls the at least one of the position of the exit pupil or the angle of incidence of the converging light based on a history of the tracking information to anticipate the gaze angle of the eye of the viewer.

8. The system of claim 1, wherein the optical subsystem directs the converging light along a configurable optical path between the optical subsystem and the pupil of the eye determined by the control subsystem.

9. The system of claim 8, wherein:
    the control subsystem determines:
        a direction in which the converging light is to be directed; and
        an apparent location from which the converging light is to be directed; and
    the configurable optical path is based at least in part on the direction and the apparent location.

10. The system of claim 1, wherein:
    the at least one desired position of the exit pupil relative to the pupil of the eye of the viewer is applicable to a plurality of viewers; or
    the at least one desired angle of incidence of the converging light relative to the pupil of the eye of the viewer is applicable to the plurality of viewers.

11. The system of claim 1, wherein:
    the at least one desired position comprises a desired position for each of a plurality of aberration types;

the at least one desired angle of incidence comprises a desired angle of incidence for each of the plurality of aberration types; and the control subsystem generates at least one of a single desired position or a single desired angle of incidence based on a combination of at least one of:

the desired position for each of the plurality of aberration types; or the desired angle of incidence for each of the plurality of aberration types.

12. The system of claim 11, wherein:

the combination comprises a linear combination of a plurality of basis functions; and each of the plurality of basis functions corresponds to one of the plurality of aberration types.

13. A method comprising:

generating, by a light source, light for an image;

receiving, by an optical subsystem, the generated light from the light source;

generating, by the optical subsystem based on the received light, converging light defining an exit pupil that includes the image;

storing, in a memory device, configuration data that indicates at least one of:

at least one desired position of the exit pupil relative to a pupil of an eye of a viewer to reduce aberration of the image that is caused by the eye of the viewer; or at least one desired angle of incidence of the converging light relative to the pupil of the eye of the viewer to reduce the aberration; and controlling, by a control subsystem, at least one of the light source or the optical subsystem to reduce the aberration by altering, based on the configuration data, at least one of:

a position of the exit pupil relative to the pupil of the eye of the viewer; or an angle of incidence of the converging light relative to the pupil of the eye of the viewer.

14. The method of claim 13, wherein controlling the light source comprises: altering the light generated by the light source to modify the image to reduce the aberration.

15. The method of claim 14, wherein, to reduce the aberration, the control subsystem alters at least one of:

a chromatic alignment of the light generated by the light source; or a geometric alignment of the light generated by the light source.

16. The method of claim 13, wherein:

the method further comprises generating, using an eye-tracking subsystem, tracking information indicating a gaze angle of the eye of the viewer; and controlling, by the control subsystem, the at least one of the position of the exit pupil or the angle of incidence of the converging light is further based on the tracking information.

17. The method of claim 16, wherein:

controlling, by the control subsystem, the at least one of the position of the exit pupil or the angle of incidence of the converging light is further based on a history of the tracking information to anticipate the gaze angle of the eye of the viewer.

18. A non-transitory computer-readable medium comprising:

computer-readable instructions that, when executed by at least one processor of a display device, cause the display device to:

generate, by a light source of the display device, light for an image;

receive, by an optical subsystem of the display device, the generated light from the light source;

generate, by the optical subsystem based on the received light, converging light defining an exit pupil that includes the image;

store, in a memory device of the display device, configuration data that indicates at least one of:

at least one desired position of the exit pupil relative to a pupil of an eye of a viewer to reduce aberration of the image that is caused by the eye of the viewer; or at least one desired angle of incidence of the converging light relative to the pupil of the eye of the viewer to reduce the aberration; and control at least one of the light source or the optical subsystem to reduce the aberration by altering, based on the configuration data, at least one of:

a position of the exit pupil relative to the pupil of the eye of the viewer; or an angle of incidence of the converging light relative to the pupil of the eye of the viewer.

19. The non-transitory computer-readable medium of claim 18, wherein the computer-readable instructions, when executed by the at least one processor, further cause the display device to alter at least one of a chromatic alignment or a geometric alignment of the light generated by the light source to reduce the aberration.

20. The non-transitory computer-readable medium of claim 18, wherein the computer-readable instructions, when executed by the at least one processor, further cause the display device to:

generate, using an eye-tracking subsystem, tracking information indicating a gaze angle of the eye of the viewer; and alter the at least one of the position of the exit pupil or the angle of incidence of the converging light further based on the tracking information.

\* \* \* \* \*